United States Patent [19]

Smith

[11] 4,383,837

[45] May 17, 1983

[54] EFFICIENT METHANE PRODUCTION WITH METAL HYDRIDES

[75] Inventor: Robert H. Smith, Plano, Tex.

[73] Assignee: Atlantic Richfield Company, Los Angeles, Calif.

[21] Appl. No.: 108,203

[22] Filed: Dec. 28, 1979

[51] Int. Cl.$^3$ ............................ C07C 1/04; C10L 3/00
[52] U.S. Cl. .................................. 48/197 R; 423/248; 423/644; 423/645; 423/648 R; 518/704; 518/705; 518/706
[58] Field of Search ........... 423/248, 644, 645, 648 R, 423/655, 656; 518/704, 705, 706; 48/197 R, 203

[56] References Cited

U.S. PATENT DOCUMENTS 3,793,435  2/1974  Reilly et al. ...................... 423/644
3,872,025  3/1975  Singleton ........................ 518/704 X

FOREIGN PATENT DOCUMENTS 50-115691  9/1975  Japan .................................. 423/248

*Primary Examiner*—Howard T. Mars
*Attorney, Agent, or Firm*—M. David Folzenlogen

[57] ABSTRACT

This invention concerns an efficient, high recovery, single product, multiple-stage process for producing high BTU methane from a low BTU feed gas containing carbon monoxide, hydrogen, nitrogen and other materials. In the process, impurities like hydrogen sulfide and carbon dioxide are removed at the appropriate point. The carbon monoxide is removed and split into two streams. One stream is reacted with steam to provide additional hydrogen which is mixed with the other carbon monoxide stream and passed to a methanator. The hydrogen in the feed gas is recovered in an especially efficient two stage manner which is suitable for use with standard cooling water and which reduces metallurgical problems, compression requirements and heat requirements. In the first stage, metal hydrides are formed, thereby separating the hydrogen in the feed gas from nitrogen and the nitrogen exits and is removed. The hydrides are then decomposed to generate additional hydrogen which is also passed to the methanator where carbon monoxide and hydrogen are reacted to form methane and water. The process produces a pipeline quality synthetic natural gas.

10 Claims, 1 Drawing Figure

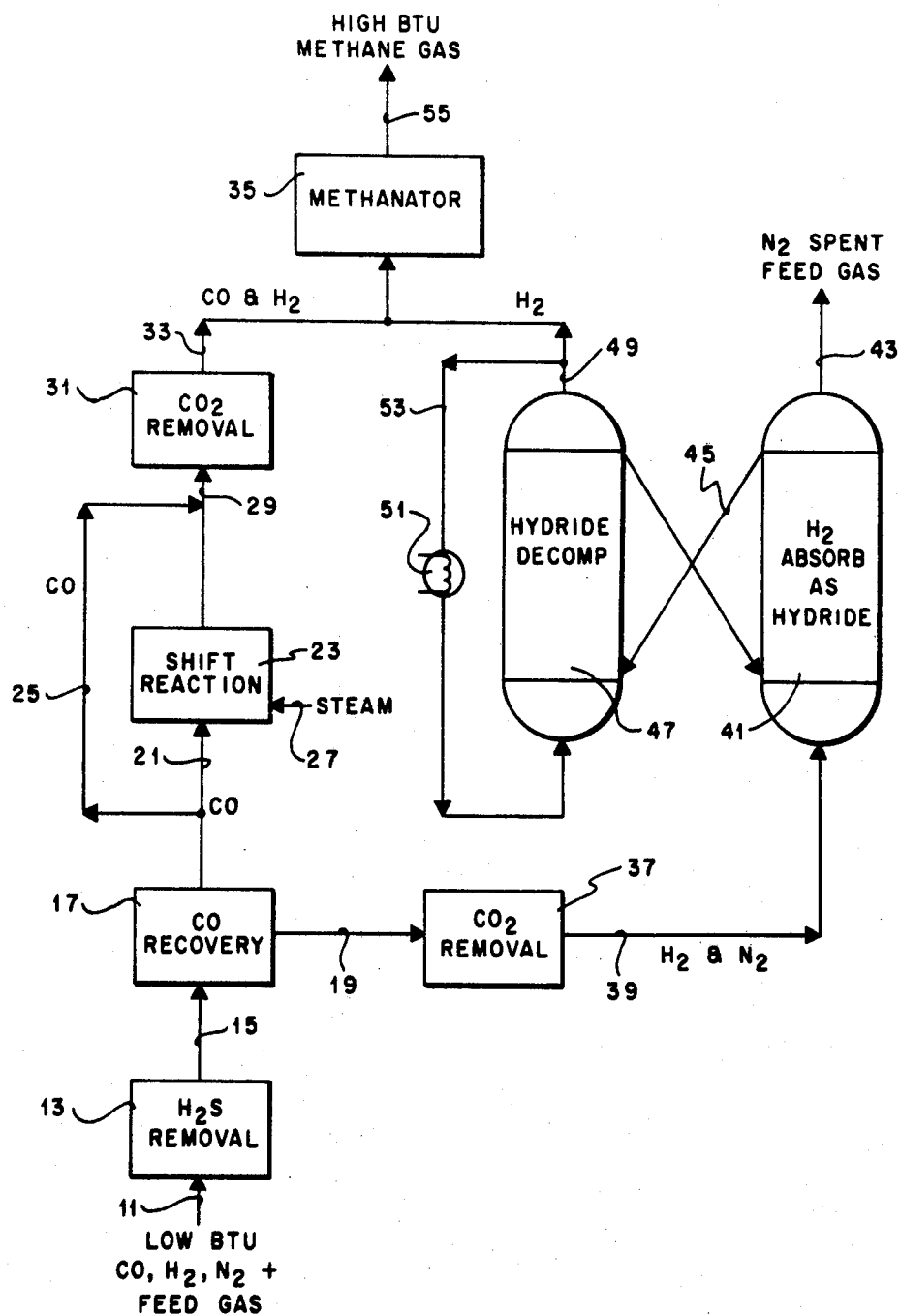

EFFICIENT METHANE PRODUCTION WITH METAL HYDRIDES

BACKGROUND OF THE INVENTION

This invention pertains to an efficient, high recovery, single product process for converting low BTU gas to high BTU methane gas using a unique combination of known processes. More particularly, high purity methane is produced by standard methanation of a balanced carbon monoxide-hydrogen feed gas derived from a unique combination of steps involving separating carbon monoxide first and then generating hydrogen in two separate ways, that is, by hydride formation and decomposition and by water-gas shift reaction of some of the carbon monoxide.

This disclosure relates to a process for producing methane from a gas containing hydrogen, carbon monoxide, nitrogen and the other components normally found in the gas produced by the gasification of carbonaceous materials with air. This gaseous product is sometimes called producer gas. By way of example, a producer gas produced from the gasification of coal may contain on a dry basis 15% hydrogen, 29% carbon monoxide, 50% nitrogen, 5% carbon dioxide and 1% methane.

The shortage of natural gas, which is predominantly methane, has greatly increased the need for economic production of synthetic natural gas. Gasification of carbonaceous materials, for example coal, produces a low BTU gas generally having a fuel value below 300 BTU per standard cubic foot, which is too low for most natural gas uses. Methane has a heat of combustion of 1013 $BTU/ft^3$. A large number of processes have been proposed for enhancing the heat value of low BTU gases. Many of these processes produce what is called an intermediate BTU gas.

The low BTU gases are hydrogen deficient for methane production. Moreover, the heating value is low if the nitrogen is not removed. The economics is also affected by the number of reactions, and gas treating and separation steps required to produce a high methane content gas. This is affected by the purity of the various reaction streams and final product.

Accordingly, it is an object of this invention to provide a method of producing a high BTU product in a way that effectively uses the carbon monoxide and hydrogen in the feed gas, that separates nitrogen during hydrogen production, that tends to produce a single methane product, that produces a final product that requires no further treatment except water removal, and that uses less energy to separate and produce hydrogen from the producer gas.

SUMMARY OF THE INVENTION

A feed gas containing carbon monoxide (CO), hydrogen ($H_2$) and nitrogen ($N_2$) is processed to produce a high BTU methane rich gas in a way that very high recoveries, for example, 95% or more, of the carbon monoxide and hydrogen are obtained. The methane product gas is formed in a standard CO-$H_2$ methanation zone using high quality CO from the feed gas and $H_2$ from two sources, thereby producing a methane fuel product. The first source of hydrogen for this reaction is obtained by separating the CO from the feed gas and reacting some of the CO in a standard water-gas shift reaction. Carbon dioxide is then removed from the $CO_2$ and $H_2$ shift reaction products to produce a high quality first source of hydrogen. The second source of hydrogen is obtained in a unique manner by absorbing $H_2$ from the feed gas as a metal hydride and then decomposing the hydride to produce a high quality second source of hydrogen. This stage of the process also removes unwanted nitrogen. The hydride formation and decomposition is especially useful for reducing cooling, heating and metallurgical problems and compression costs, and at the same time, providing high quality hydrogen for methane formation. Preferably, the hydride is formed at a temperature above 100° F. and is decomposed at a temperature below 85° F.

The feed gas will usually also contain hydrogen sulfide ($H_2S$) and carbon dioxide ($CO_2$). When these gases are present, the process will preferably include the step of first removing $H_2S$. The carbon dioxide may be removed with the $H_2S$ or removed separately after separation of the CO from the feed gas. The methane product is easily dried.

By this means, the mole ratio of $H_2$ to CO for the methanation stage is in the proper range and there are no undesirable side reactions, impurities or low BTU diluents in the product gas.

BRIEF DESCRIPTION OF THE DRAWING

A schematic representation of a preferred process configuration for producing a high BTU methane gas according to the invention is illustrated in the accompanying drawing.

DETAILED DESCRIPTION

The following description of the process for producing high BTU methane gas from low BTU producer-type feed gas focuses on a particular sequence of known process steps or stages carried out in a way that tends to produce a single high quality methane product and that does not result in loss of any of the CO and $H_2$ in the feed gas. By way of overview, the feed gas sequence is, (1) carbon monoxide removal and recovery as a separate stream, and (2) hydrogen removal by hydride formation and production of a high quality first hydrogen stream by hydride decomposition. The first hydrogen stream is then passed to a methanator. Carbon monoxide must be removed first as it would interfere with the hydride stage. The carbon monoxide stream is divided. One part is used to produce additional hydrogen by the water-gas shift reaction. The other part is used for methanation. After acid gas removal to purify the hydrogen, this additional hydrogen and the carbon monoxide are combined with the first hydrogen stream in appropriate proportion for methanation, for example a hydrogen to carbon monoxide ratio of 3.

Since low BTU gases derived from coal and some other carbonaceous fuels contain $H_2S$ and $CO_2$, the process hereinafter described in detail will also allow for the presence of these unwanted materials. Accordingly as shown in the drawing, a low BTU feed gas comprised of CO, $CO_2$, $H_2S$, $H_2$ and $N_2$ in line 11 is passed through $H_2S$ removal zone 13 where $H_2S$ is removed from the feed gas by any of the known techniques for sorption in liquids or on solid bodies without significant removal of carbon monoxide and hydrogen in the feed gas. For example, this step may be accomplished with activated charcoal and zinc oxide or with the Selexol process described in the Oil and Gas Journal for Nov. 18, 1974. In this stage of the process, $CO_2$ may also be removed if the removal of CO may be avoided;

but generally it is best to not attempt $CO_2$ removal at this time.

After $H_2S$ removal, the remaining feed gas is passed through line 15 to carbon monoxide removal and recovery zone 17 where carbon monoxide is separated from the feed gas to produce a first $H_2$-rich stream in exit line 19. Any suitable conventional process may be used for separating the carbon monoxide from the rest of the low BTU feed gas. Cryogenic cooling or physical absorption with copper ammonium acetate or cuprous aluminum chloride solutions in an absorption column may be employed. Generally, absorption is carried out at temperatures below 100° F. and pressures between 50 to 60 atmospheres. After absorption, heating (for example to 170° F.) and changing the pressure (for example, 50 or more atmospheres) of the copper liquor releases a relatively high quality carbon monoxide. After the desorption step, the resulting CO-rich stream in line 21 is divided into two streams. One stream is passed to water-gas shift reaction zone 23. The other stream bypasses the shift reactor through line 25.

Carbon monoxide in line 21 enters water-gas shift reaction zone 23 and is combined with water or steam from line 27 in the appropriate ratio to react and produce $H_2$ and $CO_2$ which leaves the shift reactor through line 29. The shift reactor is a conventional catalytic water-gas reaction zone. The water-gas shift reaction of CO and $H_2O$ is well known. Water-gas shift catalysts are typically a combination of the oxides of one or more metals like iron, chromium, cobalt, molybdate, copper, zinc, potassium, berium, antimony, uranium, or thorium. Typical reaction temperatures are between 500° F. and 1050° F. The amount of carbon monoxide reacted in the shift zone depends on the amount of carbon monoxide available for methanation, the amount of hydrogen separated from the feed gas as hereinafter described, and the desired ratio of hydrogen to carbon monoxide for the methanation zone, e.g. 3.0.

As shown, the carbon monoxide bypass stream in line 25 is combined with the $H_2$ and $CO_2$ shift reaction product in line 29 and the mixture passed through $CO_2$ removal zone 31. It may not be necessary to treat the bypass carbon monoxide; but the carbon monoxide from CO recovery zone 17 may contain a small amount of carbon dioxide and other impurities. It is, therefore, usually best to treat the CO-rich bypass stream. In $CO_2$ removal zone 31, carbon dioxide and other impurities are removed from the shift reaction products and carbon monoxide by scrubbing or passing the gases through a regenerated absorption solution or solid, or by chemical conversion to another compound. Any conventional carbon dioxide process that does not remove carbon monoxide and hydrogen may be used. For example, carbon dioxide may be removed using di- or mono-ethanolamine, hot potassium carbonate, propylene carbonate, tetrahydrothiophene dioxide and alkanolamine, or polyglycol-ether. The water in the shift reaction products is easily removed.

Leaving $CO_2$ removal zone 31 is a high quality mixture of carbon monoxide and hydrogen which flows through methanator inlet line 33 into methanator 35.

The feed gas in line 19 leaving CO recovery zone 17 is passed through second conventional $CO_2$ removal zone 37 to produce in line 39 second $H_2$-rich stream which is comprised primarily of only hydrogen and nitrogen.

This second $H_2$-rich stream is treated in a special hydride formation unit 41 to separate the feed gas hydrogen from nitrogen. This undesirable nitrogen diluent gas has no heat value and is removed through line 43 with spent producer gas. In the hydride formation unit, the $H_2$-rich gas is treated in a dilute phase, moving bed, fluid bed or fixed bed of solids where the hydrogen reacts with a metal, including metal alloys, to form hydrides. Active metals like lithium, sodium, potassium, rubidium, magnesium and calcium, and alloys such as magnesium-nickel, Mischmetal-nickel-aluminum, strontium, barium, iron-titanium, titanium-iron-nickel, lanthanum-nickel or cobalt or nickel-aluminum or nickel-copper, and praseodyonium-cobalt titanium-iron-nickel, form hydrides. Hydride formation is an exothermic reaction. It is highly desirably that at least 90% of the hydrogen react to form hydrides at a temperature above 100° F. at a reasonable rate. This provides the desired yield while allowing extraction of the exothermic heat with standard cooling water. This reduces cooling costs and problems that would be encountered if the water needed to be chilled to maintain a reactor temperature below 100° F.

The hydride formed in the hydride formation unit is decomposed. The transfer of the hydrides to the decomposition reaction zone 47 may be accomplished in any conventional technique depending on the type bed used in the hydride formation unit, for example, switching units in a fixed bed system. In the drawing, a fluid bed system is illustrated and the hydrides are passed from unit 41 through line 45 into hydride decomposition unit 47 where the hydrides are decomposed with heat to release a high quality $H_2$-rich gas through line 49 where at least a portion of the hydrogen is passed to methanator 35 with the CO and $H_2$ previously discussed. For most efficient operation, the hydride will decompose at a temperature below 850° F. and at an equilibrium pressure suitable for the methanation zone. This avoids the metallurgical problems created by high temperature hydrogen gas while providing the required yield. In addition, hydride decomposition is an endothermic reaction. Higher temperatures would require more heat input or energy consumption by the process. For illustration purposes, side heater 51 is shown for heating recycle stream 53 which is used to fluidize the decomposition bed.

For the process of this disclosure, some metal hydrides are far superior to others. The inlet of hydride formation unit 41 is connected at one phase in the system where certain pressure and temperature conditions prevail. The outlet of decomposition unit 47 is connected to a different set of operating conditions. For most efficient operation, the active metal will react at least 90% of the hydrogen in the feed gas in a reasonable time to form hydrides at one set of conditions close to the inlet feed conditions and at a temperature above 100° F. which is suitable for ordinary cooling water control. This metal hydride would decompose at another set of conditions suitable for the methanation reaction. The outlet pressure would allow transfer of the hydrogen to the methanation zone without compression and at a temperature which reduces the chances of metallurgical problems, for example, 850° F. Each particular metal hydride will exhibit a hydrogen vapor pressure or equilibrium pressure which increases with temperature. In the decomposition unit, the gas in equilibrium with the hydride is mostly hydrogen. In other words, the more effective hydrides will exhibit the desired pressure at 100% decomposition at a temperature below 850° F. In the hydride formation unit, for efficient design purposes, the hydrogen vapor pressure of the hydride may be considered as 0.1 of the inlet hydrogen partial pressure, or less, that is, at least 90% by volume of the hydrogen is reacted at a temperature above 100° F. The active metals found best for the process of this disclosure are alloys of magnesium-nickel, Mischmetal-nickel-aluminum, titanium-iron-nickel, lanthanum-cobalt, lanthanum-cobalt-nickel, and lanthanum-nickel-aluminum in the following specific ratios: $Mg_2Ni$, $MNi_{4.5}Al_{0.5}$, $TiFe_{0.8}Ni_{0.2}$, $LaCo_5$, $LaCo_4Ni$, and $LaNi_4Al$. Mischmetal is a crude alloy of rare earth metals, principally corium and lanthanum. Metal hydrides tend to disintegrate in fluid or moving bed systems. It is, therefore, preferred that the active metal be deposited or formed on a high surface area strong support material. For purposes of this invention, the support material is not considered an active metal or part of the hydride.

The system just described supplies two sources of $H_2$-rich gas to methanator 35. One stream contains carbon monoxide and hydrogen. The other stream contains only hydrogen. This allows the reaction mixture of CO and $H_2$ in methanator 35 to be adjusted to any desired $H_2/CO$ ratio for methane formation, for example 3.0. In the methanation formation zone, therefore, a high BTU single product methane gas and water is produced in product line 55. The water is readily removed. Any conventional single or multiple stage process for forming methane from carbon monoxide and hydrogen may be used. In this process, since the reactants are of high quality and in the appropriate ratio, methane may readily be formed in one stage. Multiple beds may be used for temperature control. As used herein, methanation is a catalytic reaction between carbon monoxide and hydrogen to produce methane according to the following equation:

$$CO + 3H_2 = CH_4 + H_2O + \text{heat} \qquad (1)$$

Much has been written on this process. The process is typically carried out by passing the gaseous reactants through a bed of catalyst, for example, nickel or nickel alloyed with platinum, or by fluidizing the catalyst at temperatures between 600° and 1300° F. and at pressures above 200 psig. Space velocities vary over a wide range and usually between 1800 and 12,000 v/v/hr.

EXAMPLE

A low BTU feed gas is processed in accordance with the process of this invention without $H_2S$ removal zone 13 and $CO_2$ removal zone 37 with the results shown in Table 1.

TABLE 1

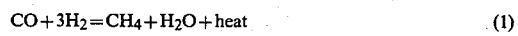

| Line No. | Temp. °F. | M Moles Per Hr. | Mole Percent | | | | | |
|---|---|---|---|---|---|---|---|---|
| | | | H₂O | N₂ | CO | CO₂ | H₂ | CH₄ |
| 11 | 100 | 250 | — | 46.8 | 17.5 | 13.0 | 21.0 | 1.7 |
| 19 | 300 | 206.7 | — | 56.6 | 0.2 | 15.7 | 25.4 | 2.0 |
| 43 | 300 | 154.7 | — | 75.6 | 0.3 | 21.0 | 0.3 | 2.7 |
| 49 | 800 | 52 | — | — | — | — | 100 | — |
| 21 | 100 | 19.8 | — | — | 100 | — | — | — |
| 25 | 100 | 23.5 | — | — | 100 | — | — | — |
| 27 | 100 | 79.0 | 100 | — | — | — | — | — |
| 29 | 650 | 98.8 | 60.2 | — | — | 19.5 | 19.5 | — |
| 33 | 200 | 30.7 | — | — | 1.3 | 4.7 | 94.0 | — |
| 55 | 550 | 49.6 | 42.2 | — | — | 2.7 | 8.3 | 46.8 |

After removing the water, the final product gas is 80.85 mol percent methane, 14.38 mol percent hydrogen, 4.7 mol percent carbon dioxide and 0.07 mol percent carbon monoxide.

Reasonable variations and modifications are possible within the scope of this disclosure without departing from the spirit and scope of this invention.

The embodiments of the invention in which an exclusive property or privilege is claimed are defined as follows:

1. A process for producing methane from a feed gas comprised of $H_2$, CO and $N_2$, said process comprising.
   (a) removing CO from said feed gas to produce a first $H_2$-rich gas;
   (b) dividing the CO separated in step (a) into a first and a second CO-rich gas;
   (c) reacting said first CO-rich gas produced in step (b) with $H_2O$ in a water-gas shift conversion zone to produce a gas rich in $CO_2$ and $H_2$;
   (d) removing $CO_2$ from the gas produced by step (b) to produce a second $H_2$-rich gas;
   (e) passing said second $H_2$-rich gas to a methane forming reaction gas;
   (f) reacting $H_2$ in said first $H_2$-rich gas produced in step (a) with a solid material comprised of at least one active metal to form a hydride thereby producing spent waste gas rich in $N_2$;
   (g) decomposing hydride produced in step (f) to form a third $H_2$-rich gas;
   (h) passing said second CO-rich gas produced in step (b) to said methane forming reaction gas;
   (i) passing at least a portion of said third $H_2$-rich gas to said methane forming reaction zone, and
   (j) reacting said gases passed to said methane forming reaction zone to produce methane.

2. In the process of claim 1 wherein said feed gas also contains $H_2S$ and prior to step (a), $H_2S$ is removed from said feed gas.

3. In the process of claim 1 wherein said feed gas also contains $CO_2$ and after step (a) but prior to step (f), $CO_2$ is removed from said first $H_2$-rich gas.

4. In the process of claim 3 wherein said feed gas also contains $H_2S$ and prior to step (a), $H_2S$ is removed from said feed gas.

5. In the process of claim 1 wherein prior to step (d), said second CO-rich gas is combined with said gas rich in $CO_2$ and $H_2$ produced in step (c).

6. In the process of claim 5 wherein said feed gas also contains $CO_2$ and after step (a) but prior to step (f), $CO_2$ is removed from said first $H_2$-rich gas.

7. In the process of claim 6 wherein said feed gas also contains $H_2S$ and prior to step (a), $H_2S$ is removed from said feed gas.

8. In the process of claim 1 wherein the hydride reaction of step (f) is carried out at a temperature above 100° F. and decomposition of the hydride in step (g) is carried out at a temperature below 850° F.

9. In the process of claim 1 wherein in step (f) said solid material is comprised of an active metal selected from the group consisting of $Mg_2Ni$, $MischmetalNi_{14.5}Al_{0.5}$, $TiFe_{0.8}Ni_{0.2}$, $LaCo_5$, $LaCo_4Ni$, or $LaNi_4Al$.

10. In the process of claim 9 wherein the hydride reaction of step (f) is carried out at temperature above 100° F. and decomposition of the hydride in step (g) is carried out at temperature below 850° F.

* * * * *